United States Patent [19]
Larson et al.

[11] Patent Number: 6,094,980
[45] Date of Patent: Aug. 1, 2000

[54] TORSION SPRING TESTER

[75] Inventors: David A. Larson, Isanti; William R. Dixon, Jr., Blaine, both of Minn.

[73] Assignee: Larson Systems Inc., Blaine, Minn.

[21] Appl. No.: 09/169,254

[22] Filed: Oct. 9, 1998

Related U.S. Application Data

[60] Provisional application No. 60/062,352, Oct. 15, 1997.

[51] Int. Cl.[7] ........................................................ G01L 3/00
[52] U.S. Cl. .................................................................. 73/161
[58] Field of Search .................................................. 73/161

[56] References Cited

U.S. PATENT DOCUMENTS

| | | | |
|---|---|---|---|
| 4,086,809 | 5/1978 | Wu et al. .................................... | 73/161 |
| 5,324,011 | 6/1994 | Vilches et al. ............................ | 267/156 |
| 5,650,704 | 7/1997 | Pratt et al. ................................ | 318/623 |
| 5,855,138 | 1/1999 | Curry et al. ............................... | 73/161 |

OTHER PUBLICATIONS

"Improve the Performance of Your Torsion Springs with s SRAMA Torque Testing Machine", on or about Oct., 1998.

"Digital Torsion Spring Test System" by Link Engineering Company, on or about 1990.

"Digital Torsion Spring Testers" by Carlson Electronic, The Carlson Company, pp. 5–6, on or about 1990.

*Primary Examiner*—Max Noori
*Attorney, Agent, or Firm*—Nikolai, Mersereau & Dietz, P.A.

[57] ABSTRACT

A torsion spring tester incorporates a microprocessor based data acquisition/control package and special tooling. The tooling makes calibration of the tester very easy. The combination of the tooling and control package permits acquisition, storage and transfer of test data that is accurate, absolute and repeatable.

19 Claims, 12 Drawing Sheets

TORSION SPRING TESTER

CROSS REFERENCE TO RELATED APPLICATION

The application claims the benefit of U.S. Provisional Application Ser. No. 60/062,352, filed Oct. 15, 1997.

BACKGROUND OF THE INVENTION

1. Field of the Invention

The present invention relates to a system for testing torsion springs. More specifically, the present invention relates to a torsion spring tester having dedicated fixtures which permit absolute measurements rather than relative measurements to be taken of the spring and further permits the results of such measurements to be repeatable.

2. Description of the Prior Art

A variety of torsion spring testers have been available for a number of years. These torsion spring testing machines are designed for checking torque loads in inch ounces and inch pounds and deflections in degrees. They are intended for use with a variety of springs including torsion springs, double torsion springs, spiral springs, clock springs, motor springs and power springs. Early spring testers work in conjunction with a balance and weights to determine torque load. Such units also typically included a protractor to permit one to read deflection in degrees. More recently, various companies have developed digital torsion spring testers. Such testers typically utilized a load cell and an "electronic protractor" measuring deflection. Testers of the type described above are manufactured by The Carlson Company of Clinton, Arkansas, the Spring Research and Manufacturers' Association of Sheffield, England and Link Engineering Company of Plymouth, Michigan.

Testers of the type described above offer a variety of advantages. However, set up, use and recordation of information using such testers generally tends to be time consuming. Further, the results tend not to be repeatable. As such, there is a real need for a torsion spring tester which is quick and easy to use, is quick and easy to calibrate, and is capable of providing measurements which are repeatable. There is also a real need for a torsion spring tester that provides absolute measurements rather than relative measurements.

SUMMARY OF THE INVENTION

The present invention relates to a new torsion spring tester that is easy to use, easy to calibrate, generates repeatable results and provides absolute rather than relative measurements. The system includes a carriage, a first housing secured to the carriage in a fixed position, and a second housing slidable back and forth along the carriage. The first, fixed housing contains a face plate coupled to a tube, and a microprocessor based data acquisition/control package. It also contains a specially designed load cell which measures the load and transfers the data into the electronics package. Running through the tube in the first housing is a threaded shaft which is coupled to a knob. The threaded shaft is used to couple a tooling blank to the face plate in the housing.

The second housing includes three individually positionable stops, a sliding stop bar, and a knob used to fix the stops in place. The second housing also includes a face plate coupled to a tube. A threaded shaft running through the tube is used to couple a second tooling blank to the face plate on the housing. The tube is also coupled by a belt to an encoder. The encoder is used to measure rotation of the tube. To impart rotational motion to the tube (and thus to the face plate and tooling blank), the housing is provided with two exterior knobs. These knobs are coupled to a gearing arrangement. A switch is also provided to activate one knob or the other. Since the gearing ratio associated with the two knobs are different, one of the knobs can be used for gross rotation of the tube while the other can be used for fine rotation of the tube. Signals from the encoder are transmitted via a cable to the electronics package in the first housing.

A key aspect of the present invention is the tooling that is used in conjunction with the first and second housings. As explained above, each tooling member includes a blank which is coupled using the threaded shaft to the face plate of the specific housing. The tooling secured to the second housing, in addition to the blank, includes a mandrel and a first engagement bar. The tooling secured to the first housing includes a second engagement bar. Also provided are first and second zeroing elements. The first zeroing element is a pin that can be coupled to one of the tooling blanks. The second is a slot in the other tooling blank which receives the pin. When the first and second blanks are attached to the face plates of the first and second housings, the second housing is slid toward the first housing until the pin engages the slot. Switches associated with the electronics are then used to indicate to the electronics that the device is now in the zeroed position. Once zeroing is complete, the second housing can be slid back along the carriage and the pin can be removed. A spring can then be placed over the mandrel and easily tested. The fact that the second housing incorporates three stops allows the spring to be easily tested at three preset angles of deflection.

Another key aspect of the present invention is the use of a replaceable load cell cartridge designed to be interchangeable with other load cell cartridges. This offers significant advantages. First, it broadens the number of applications for which the spring tester can be used. Second, it makes calibration of the load cells much more efficient. For example, the National Association of Spring Testing recommends that load cells be calibrated annually. Prior to the present invention, the whole machine would have to be shipped for calibration, making it unavailable for use for a significant period of time. The present invention allows the owner to merely remove and ship the cartridge. The rest of the machine can continue to be used with a replacement cartridge.

The replaceable load cell cartridges can either be "dumb" or "smart". Dumb cartridges include only a load cell. When calibrated, the performance characteristics are noted in writing so that the user can manually input those characteristics into the machine as part of the cartridge installation process. Smart cartridges include memory and input/output capabilities. Thus, parameters related to the calibration of the cartridge can be stored in memory during the calibration operation and electronically read by the machine. This serves to eliminate the need to manually input these parameters during installation of the cartridge.

Various other advantages and benefits of the present invention will become clear from a thorough reading of the following detailed description of the preferred embodiment in conjunction with the figures provided herewith.

DETAILED DESCRIPTION OF THE PREFERRED EMBODIMENTS

Figure 1:
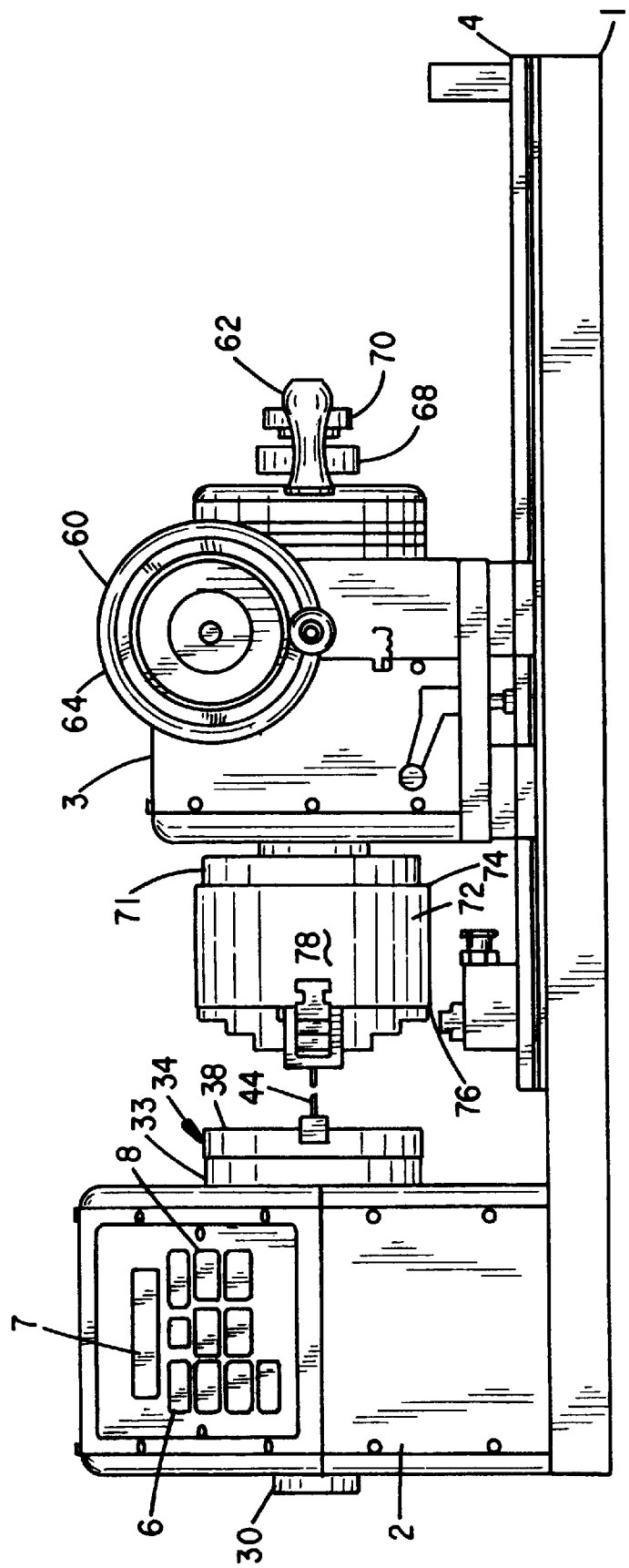
FIG. 1 is an elevational plan view of one side of the device of the present invention.
Figure 2:
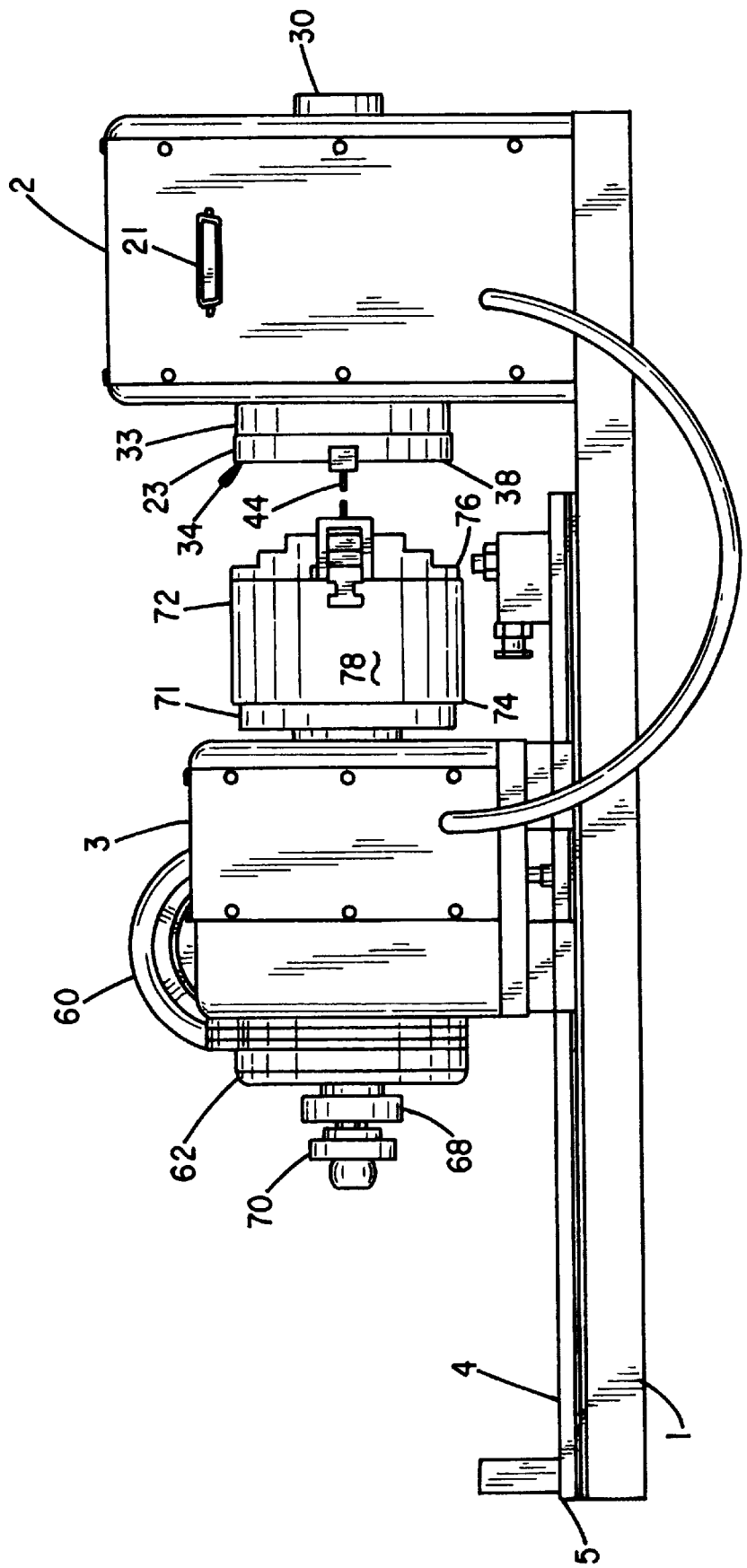
FIG. 2 is an elevational plan view of the opposite side of the device shown in FIG. 1.

FIGS. 1 and 2 are perspective views of the present invention. Shown in these figures is a carriage 1, a first housing 2 fixed in place at one end of the carriage 1, and a second housing 3 mounted to rails 4 and 5 of the carriage so that the second housing 3 can slide back and forth along the rails 4 and 5.

Figure 7:
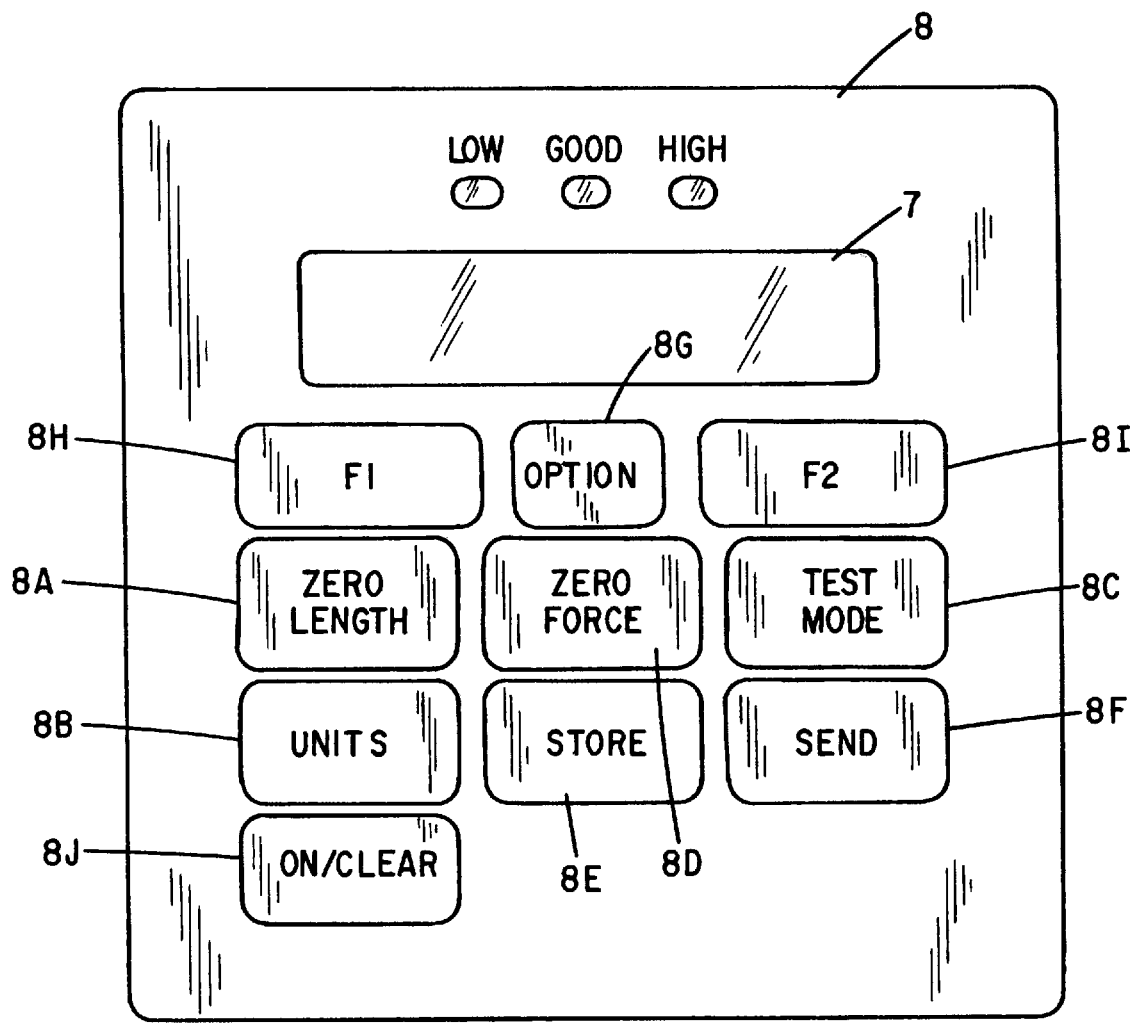
FIG. 7 is a view of a typical display and key pad arrangement.
Figure 8:
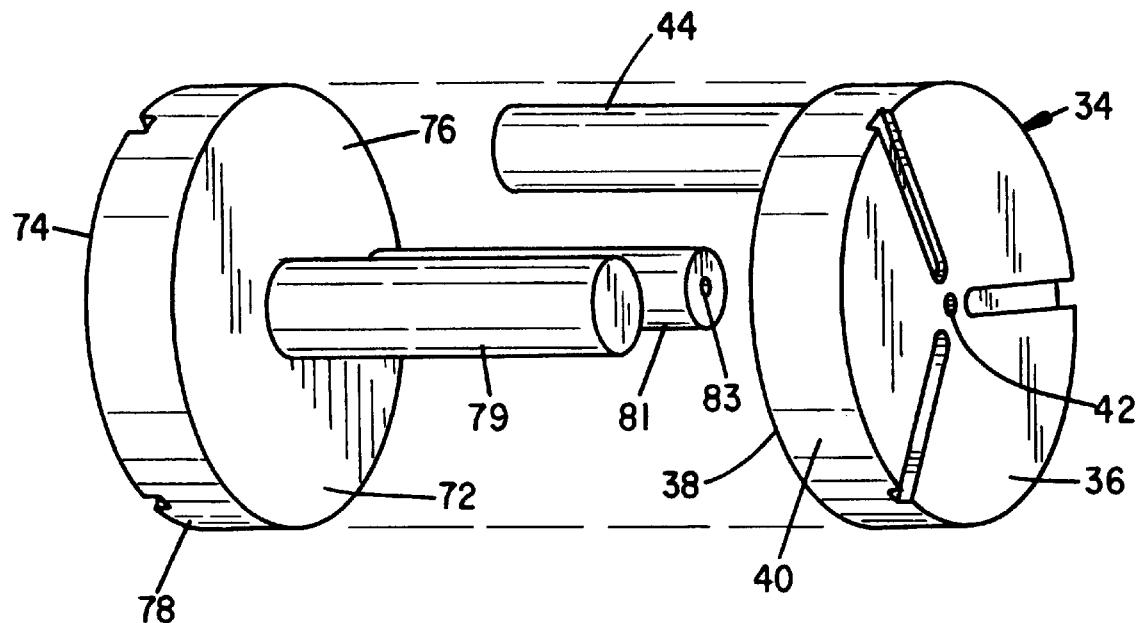
FIG. 8 is a perspective view of two typical tooling members.
Figure 9:
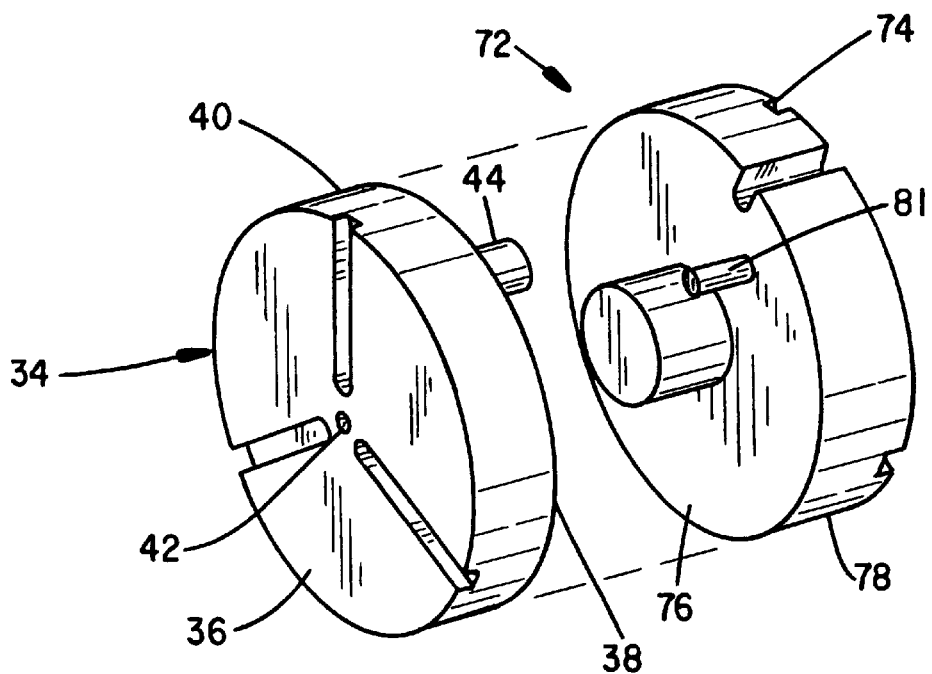
FIG. 9 is a perspective view of two alternative tooling members.

As shown in FIG. 1, the first fixed housing 2 includes a control panel 6 which includes a display 7 and a key pad 8. The display 7 is preferably a liquid crystal display. The key pad 8 preferably includes ten switches 8a–8j as shown in FIG. 7. The control panel 6 provides an interface between an electronics package 9 (see FIG. 3) and the user.

Figure 3:
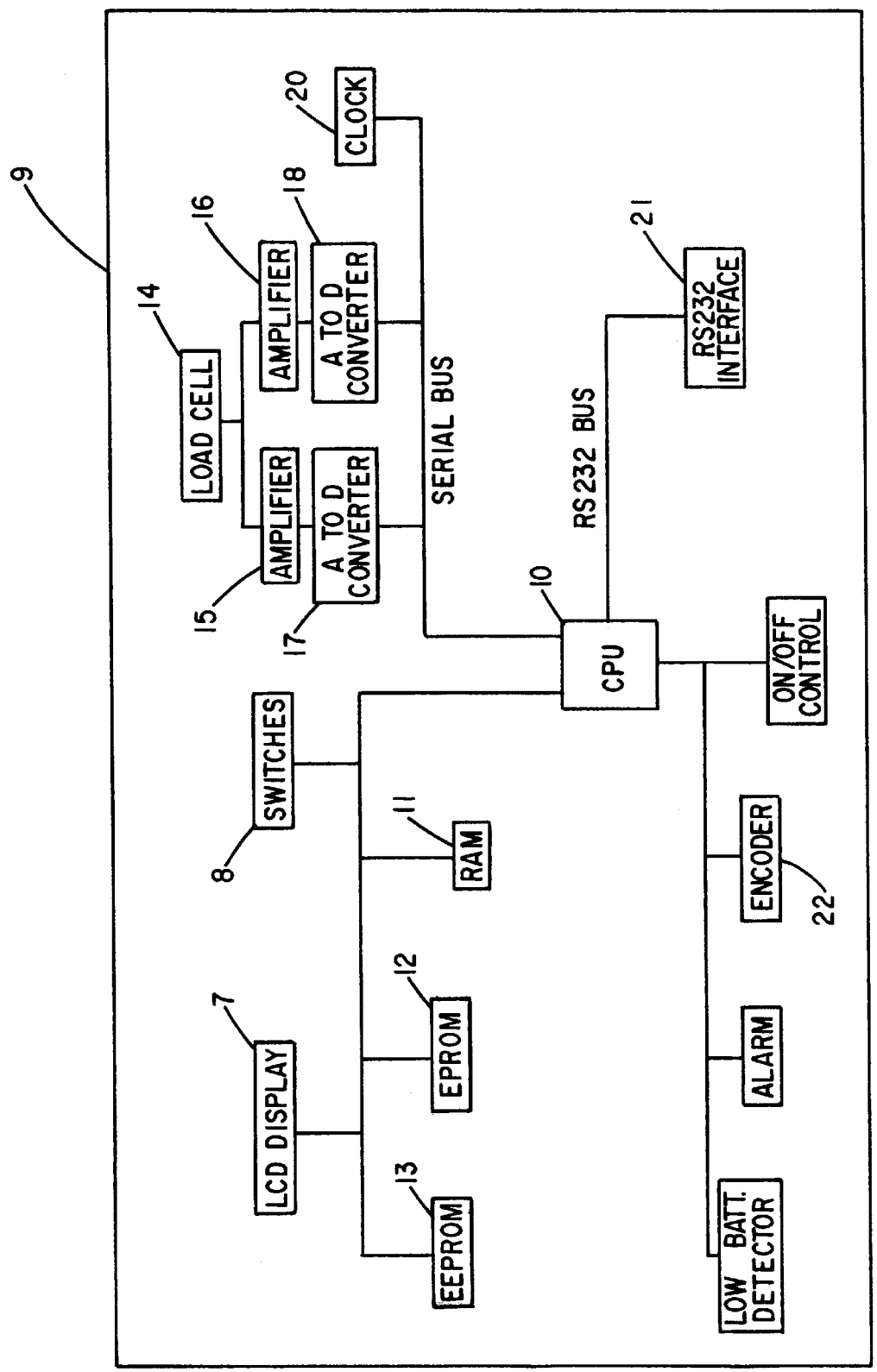
FIG. 3 is a block diagram of the electronics of the present invention.

FIG. 3 is a block diagram of the electronics package 9. As shown in FIG. 3, the electronics package 9 includes the display 7 and switches 8 which are labeled 8a–8j in FIG. 7. The electronics package also includes a microprocessor 10 and three types of memory, static random access memory (RAM) 11, electrically programmable read-only memory (EPROM) 12, and electrically erasable programmable read-only memory (EEPROM) 13. The program of instructions for controlling operation of the device is stored in the EPROM 12. Data collected by the device can be stored in the EEPROM 13.

In one embodiment, the electronics package 9 also includes a load cell 14. The load cell 14 is electrically coupled to a pair of amplifiers 15 and 16 which are, in turn, coupled to a pair of analog-to-digital converters 17 and 18 which convert the analog signals from the load cell 14 to digital signals which are forwarded to the microprocessor 10. The electronics package 9 also includes a clock 20 and an RS232 interface 21. The RS232 interface 21 can be used to electrically couple the device to a printer (not shown) or personal computer (not shown). This permits data to be printed or to be stored on a separate computer where the data can be manipulated or otherwise further processed. Another important aspect of the electronics package 9 is the encoder 22. While the encoder 22 is physically located within the second housing 3, it is hardwired to the electronics package 9 so that signals generated by the encoder 22 are received and processed by the microprocessor 10.

Figure 10:
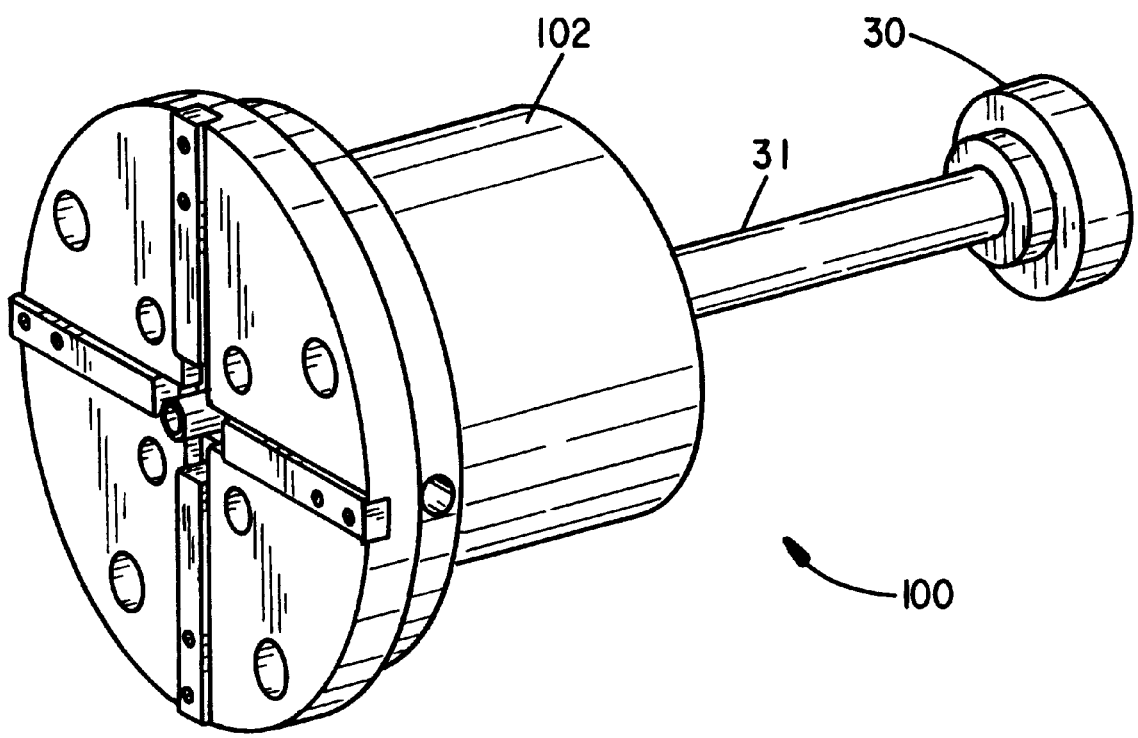
FIG. 10 is a perspective view of a load cell cartridge housing.
Figure 11:
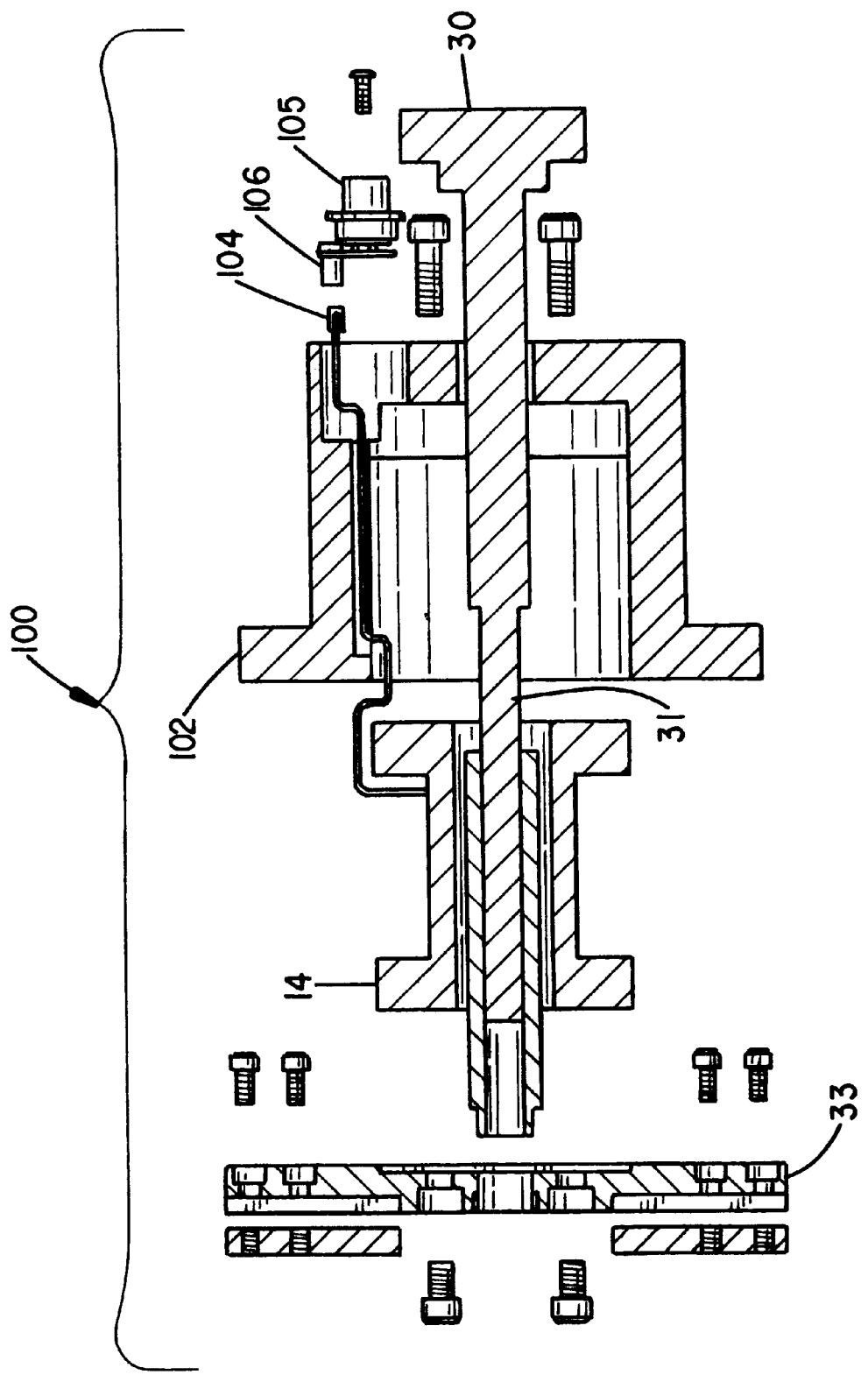
FIG. 11 is a cross-sectional view of the contents of the load cell cartridge housing of FIG. 10.
Figure 12:
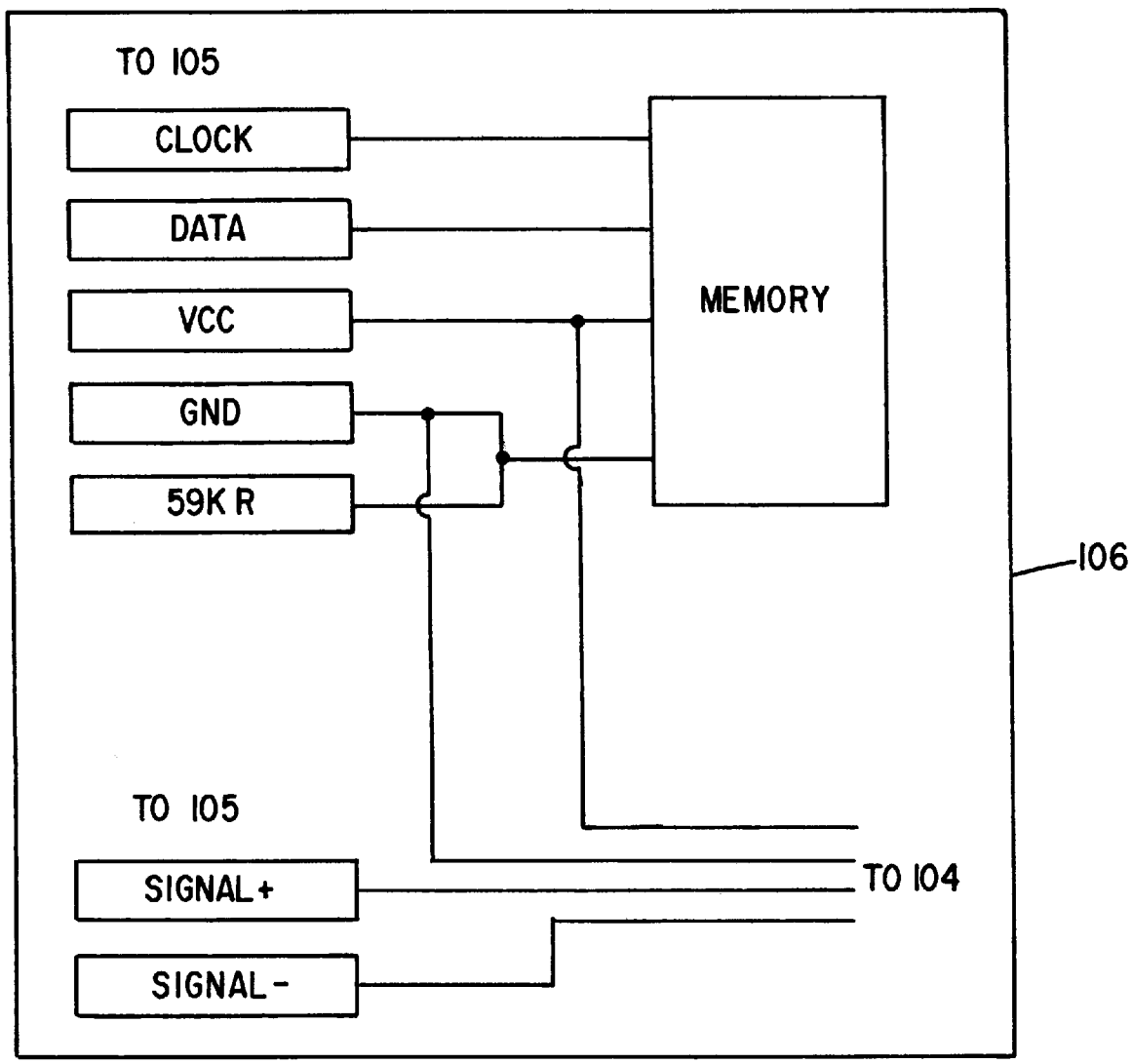
FIG. 12 is a schematic diagram of the electronics package of a smart load cell cartridge.

As an alternative to the permanent installation of a load cell 14, a load cell cartridge 100 which houses a load cell 14 can be used. See FIGS. 10–12. Such a cartridge 100 includes a housing 102 designed to allow the cartridge 100 to be physically mounted to one of the housings 2 or 3. The cartridge 100 also includes a jack 104 for electrically coupling the cartridge 100 to the rest of the electronics package 9. The housing 102 and jack 104 are both shown in FIG. 11.

Two varieties of load cell cartridges 100 are contemplated by the present invention. One is a "dumb" cartridge which includes nothing other than the load cell 14, the housing 102 which allows it to be physically coupled to either the fixed housing 2 or the slidable housing 3, and the jack 104 which carries signals generated by the load cell 14 to the rest of the electronics package 9. The other is a smart cartridge which includes all of the elements of the dumb cartridge plus a memory module 106 comprising the electronic elements shown in FIG. 12. The memory module 106 is coupled to the load cell 14 by the jack 104 and allows data relating to the performance characteristics of the load cell 14 to be electronically stored in the cartridge 100. The memory module also is capable of sending signals to the rest of the electronics package 9 via port 105.

Significant advantages are achieved through the use of interchangeable load cell cartridges 100. First, a variety of load cells rather than a single load cell 14 can be used on the same machine. This greatly increases the capability and flexibility of the machine. Also, if a plurality of cartridges are available, there is no "down time" during calibration of the load cell or need to ship the entire machine to a remote location for calibration of the load cell.

The difference between a dumb and a smart cartridge 100 relates exclusively to the manner in which load cell performance characteristics are stored and conveyed to the microprocessor 10 of the electronics package 9. When a dumb cartridge is used, such performance characteristics are entered via the key pad 8 or another data entry device, such as a personal computer, attached electrically and coupled to the electronics package 9, via the RS232 interface 21. The advantage of the smart cartridge is that these performance characteristics can be stored in the memory module 106 and transferred automatically to the microprocessor 10 of electronics package 9. Such performance characteristics can include, but are not limited to, the full scale value of the load cell 14 in the cartridge, the electrical output of the load cell 14 when zero load is being applied to the load cell 14, the electrical output of the load cell 14 when a load approximating the full scale value is applied to the load cell 14, and data that can be used by the microprocessor to linearize the output of the load cell 14.

Figure 4:
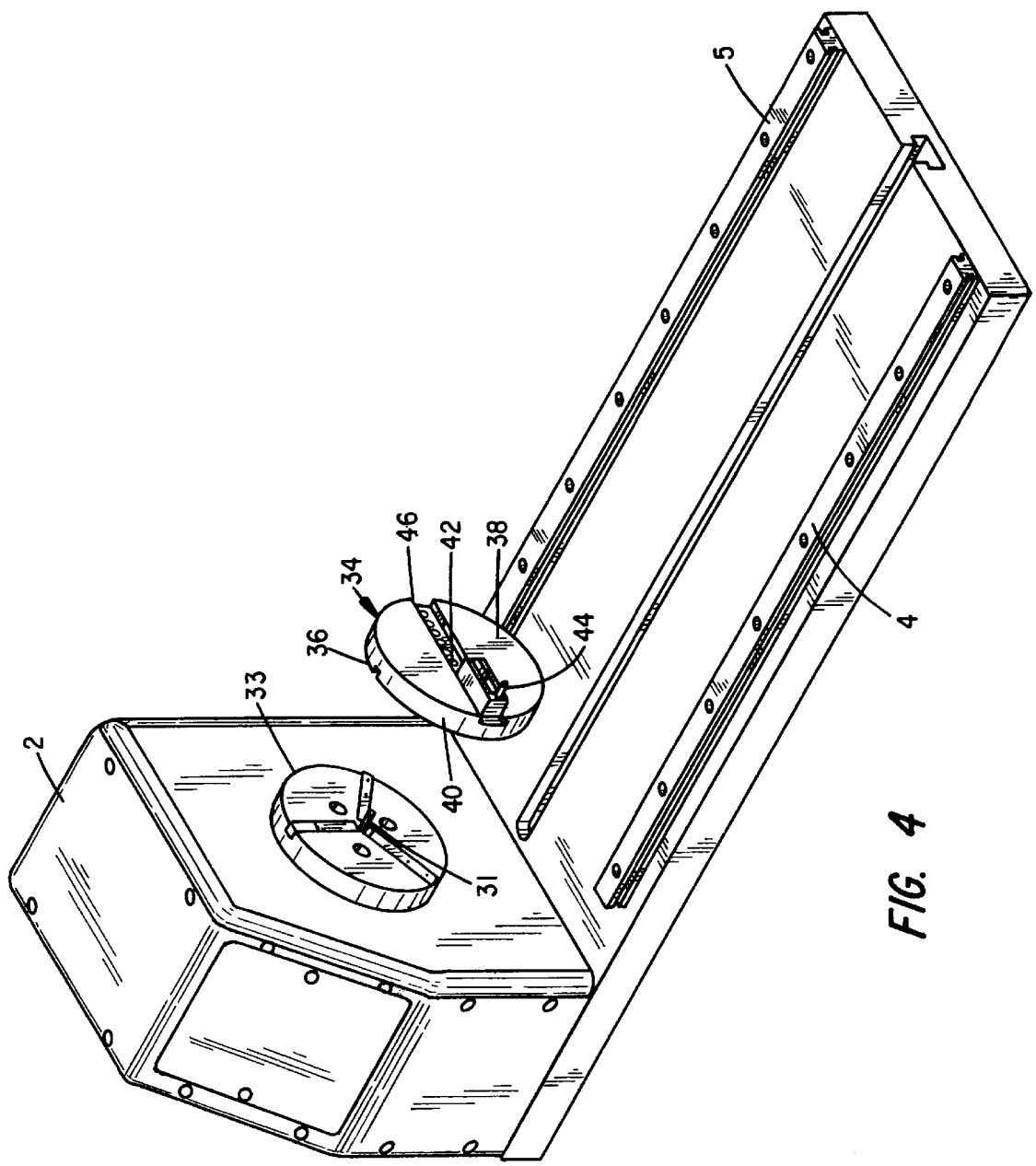
FIG. 4 is a perspective view showing various components associated with the first housing of the device shown in FIG. 1.
Figure 5:
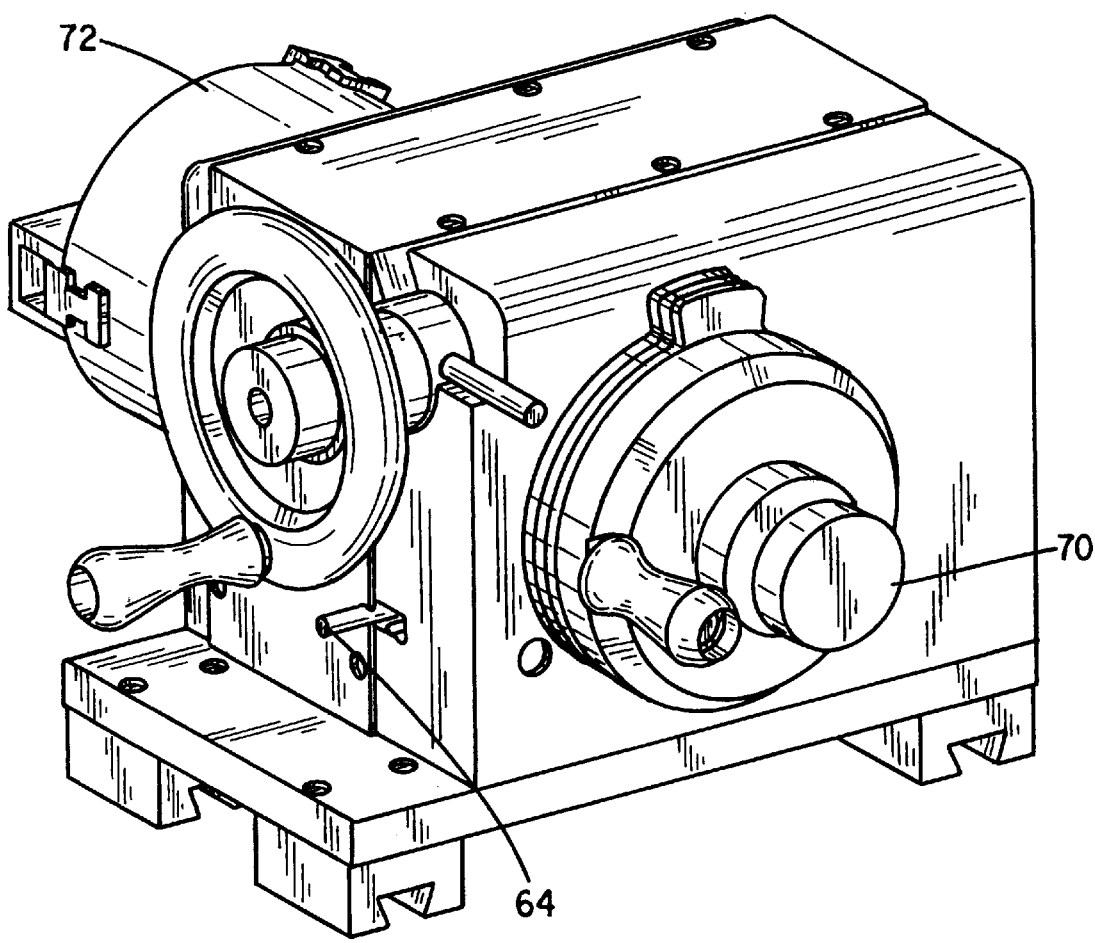
FIG. 5 is a perspective view of various components associated with the second housing of the device shown in FIG. 1.
Figure 6:
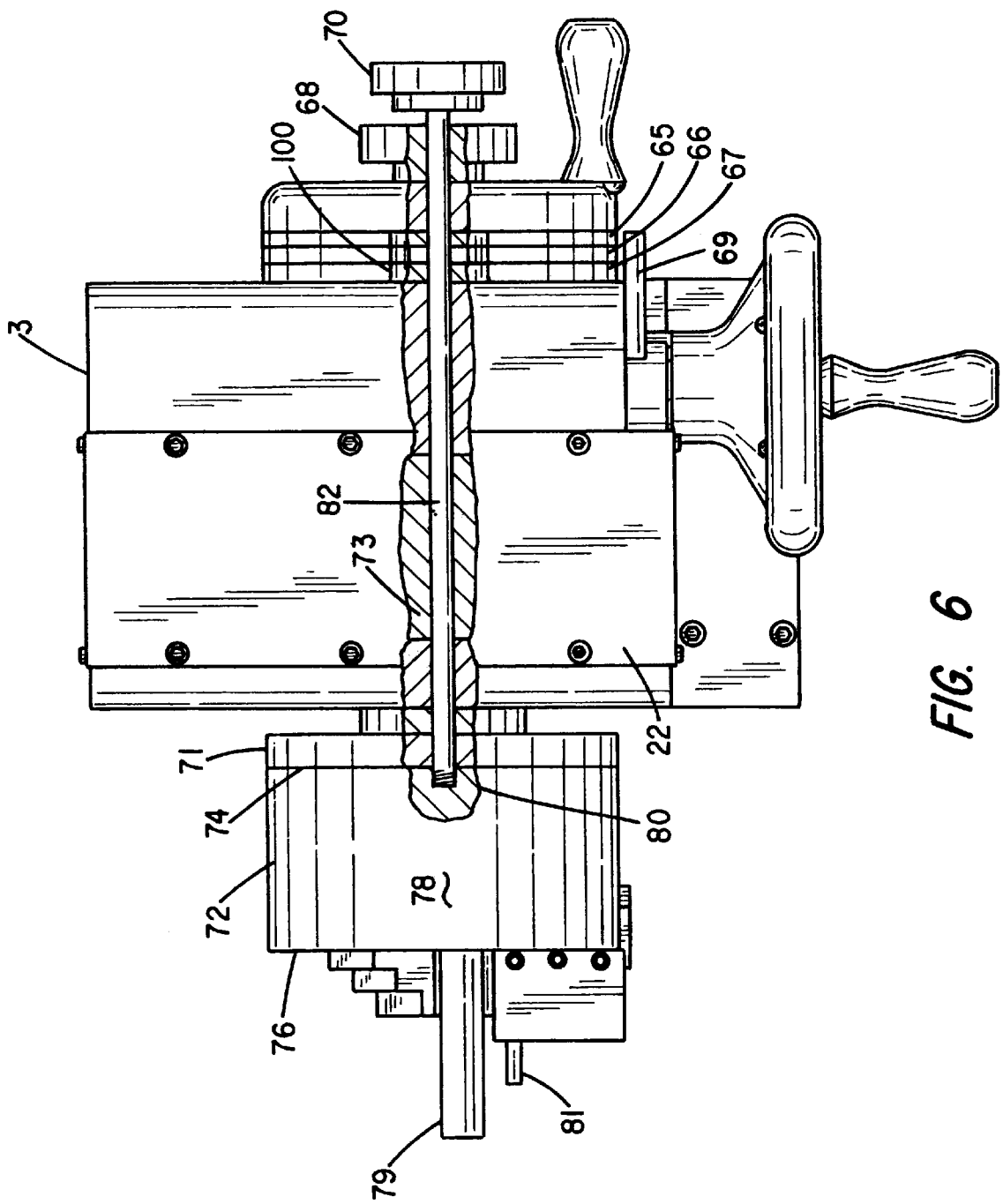
FIG. 6 is a top plan view of the second housing with portions thereof cut away to show the manner in which tooling is coupled to the housing.

Turning, then, to FIGS. 1, 2, 4, 8 and 9 associated with the first, fixed housing 2 is a knob 30 coupled to a shaft 31. The shaft 31 runs through the fixed housing and is used to join a tooling blank 34 to the face plate 33 of housing 2. The tooling blank 34 has a generally cylindrical shape including a first face 36, an opposing second face 38 and a side wall 40. Located at the center of the first face 36 is a threaded bore 42. The threaded bore 42 cooperates with threading on the shaft 31 to secure the blank 34 to the face plate 33 of the housing 2. As shown in FIG. 4, the blank 34 also has an engagement member 44 projecting perpendicularly from the second face 38 and a zeroing slot 46 in the side wall 40. The zeroing slot is open through the second face 38.

Figure 13:
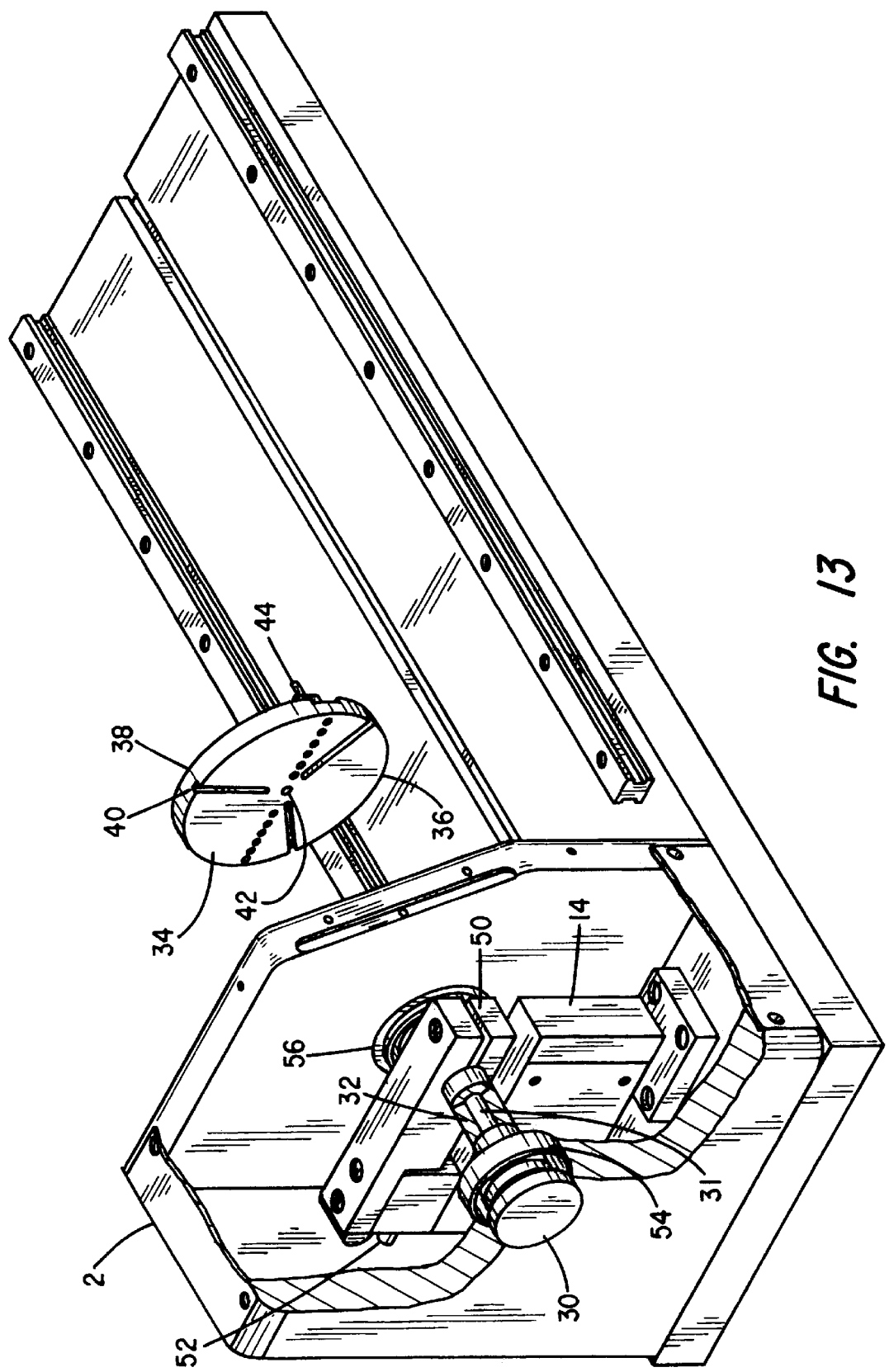
FIG. 13 is a perspective view with portions cut away to show the manner in which the load cell is actuated.

FIG. 13 shows in greater detail how the engagement member 44 interacts with the load cell 14. The engagement member 44 projects from the face 38 of the tooling blank 34. Face 36 of the tooling blank is secured to the face plate 33 of the housing by running the shaft 31 through the tube 32 coupled to the face plate 33. As such, torque is readily transferred from the engagement member 44 through the tooling blank 34 and face plate 33 of the housing to the tube 32. Coupled to the tube 32 is an arm 50. The end of arm 50 is located a distance of more than 10 thousands of an inch above the load cell 14 so that it never comes into contact with the load cell 14. A flexible metal strip 52 is attached at one of its ends to the load cell and at the other of its ends to the arm 50. This strip 52 is used to transfer torque from arm 50 to the load cell 14. Thus, the load cell 14 is only capable of measuring loads transmitted through the flexible metal strip 52. First and second bearing elements 54 and 56 secure the tube 32 and arm 50 in place and prevent them from rotating.

FIGS. 1, 2, 5 and 6 show the second housing 3. Associated with the second housing are a first wheel 60, a second wheel 62, a switch member 64, three stops 65, 66 and 67, a stop securing knob 68, a knob 70, a face plate 71 and a second tooling blank 72. Like tooling blank 34, tooling blank 72 has a generally cylindrical shape having a first face 74, a second face 76, and a cylindrical side wall 78. Located at the center of the first face 74 is a threaded bore 80. A shaft 82 (see FIG. 6) projects from knob 70 through a tube 73 joined to the face plate 71 of the housing 3. The shaft 82 has a threaded end which cooperates with the threaded bore 80 to fix the tooling blank 72 so that its face 74 is in face-to-face registration with the face plate 71 of the housing 3 and so that its face 76 is in face-to-face registration with face 38 of the first tooling blank 34. Projecting perpendicularly from the center of face 76 is a mandrel 79. Also projecting perpendicularly from the face 76 is a second engagement member 81. A zeroing pin is also provided. The zeroing pin can either be coupled to the engagement member 80 using orifice 83 (see FIG. 8) or otherwise coupled to the tooling blank 72. To zero the device, the zeroing pin is mated with the zeroing slot 46 and switches on the electronic package is actuated to signal the microprocessor 10 that the device is in the zero position.

Located within the housing 3 is a gear box (not shown). The gear box is used to impart rotational motion to the tooling blank 72 via the tube 73 and face plate 71 of the housing 3. The encoder 22 is positioned to detect movement of the tube 73 and transfer signals representative of rotation of the tube 73 to the microprocessor 10. The switch member 64 is actuated to selectively couple either the first wheel 60 or the second wheel 62 to the gear box and thus to the tube 73. The gearing is such that when the first wheel 60 is engaged (via switch member 64), it can be rotated for gross rotation of the blank 72. Alternatively, when the switch member 64 is positioned so that the second wheel 62 is engaged, wheel 62 can be turned to impart fine rotation to the blank 72. In the preferred embodiment, rotation of wheel 60 turns the blank 72 forty times further than the same rotation of wheel 62.

The housing also includes a sliding stop bar 69. See FIG. 6. Stop bar 69 is provided to engage projections on the stops 65, 66 and 67 to define the selected angles at which test readings will be taken.

The electronics package 9 and the program used in the preferred embodiment combine to offer a variety of advantages. Perhaps the most significant is the ability to compensate for deflection of the tooling blank 34 during testing of a spring. As load signals are sent to the microprocessor 10 from the load cell 14, the software performs an algorithm which calculates rotation of the tooling blank 34 from the load readings. This calculation is then used to adjust the test data related to the springs to make the deflection data more accurate.

As indicated above, the display 7 and key pad 8 provide an operator interface. See FIG. 7. For example, the key pad includes two zeroing switches, 8a to zero the torque and 8b to zero the deflection angle. The units switch 8c allows the user to tell the microprocessor to store, display and print data in either English or metric units. The store switch 8d can be used to send an instruction to the microprocessor 10 to store the data related to the test. The data is then stored in memory 13 where it can later be recalled and displayed or transmitted through the RS232 port 21 to an external computer or printer. The send switch 8e is used to instruct the microprocessor 10 to transmit the data through the RS232 port 21 to generate, for example, a hard copy printout of the data. The test mode switch 8f is used to select between various preset modes of operation. The option switch 8g and the two function switches 8h and 8i are used to set various parameters. Typically, the option switch is activated to instruct the microprocessor 10 to display various menu options and the two function switches 8h and 8i are used to select between the menu options. The on/clear switch 8j is used to both turn on the device and clear data to begin a new test.

In view of the foregoing explanation of the preferred embodiment, its operation will now be described. First, the second housing 3 is slid back along the rails 4 and 5 to separate it a working distance from the first housing 2. Second, the tooling blank 34 is positioned and secured to the face plate 33 of housing 2 by coupling the threaded end of the shaft 31 to the threaded bore 42. The knob 30 is used to secure the blank 34 in position. No separate tools are required. In a similar fashion the blank 72 is secured to the face plate 71 of the second housing 3. The threaded end of shaft 82 is coupled to the threaded bore 80 in the blank 72. The knob 70 is used to tighten the connection. Again, no additional tools are required.

Next, the zeroing pin 82 is inserted into a bore 83 in the end of engagement member 80 to temporarily couple the zeroing pin 82 to the engagement member 81. The housing 3 is slid along the rails 4 and 5 toward the housing 2. As this occurs, the blank 72 is rotated so that the zeroing pin 82 is aligned with the zeroing slot 38 in the tooling blank 34. The housing 3 is slid forward until the zeroing pin 82 rests within the zeroing slot 46. With the housing 3, tooling blank 72 and zeroing pin 82 so positioned, and with no load on the engagement member 44, the operator then depresses the two zeroing switches 8a and 8b. Thus, the microprocessor 10 is able to establish the "zero" deflection angle and torque parameters so that all measurements taken thereafter will be absolute rather than relative.

With the housing 3 still in the "zeroing position", the three stops 65, 66 and 67 can be set to establish the angle at which various test data will be recorded. These stops can be set individually using separate set screws associated with each stop. Alternatively, the stop securing knob 68 can be tightened to simultaneously lock all three stops in place. When the stop securing knob 68 is used, no special tools are required.

Once the device has been "zeroed" and the stops have been set, the housing 3 is slid along the rails away from the housing 2. The zeroing pin 82 is removed and the first spring to be tested is slid over the mandrel 79. The housing 3 is slid back toward the housing 2 and the spring to be tested is positioned so that one of its outer tines engages one of the engagement members and the other of its outer tines engages the other engagement member. With the spring so positioned, the operator actuates the switch member to 4 to select which of the two wheels 60 or 62 the operator wishes to use. The operator then turns the selected wheel to impart a rotational motion via the tube 73 and face plate 71 to the tooling blank 72. As the tooling blank 72 rotates, changes in deflection angle and load are displayed. The operator continues to rotate the wheel until the projection 100 in the first stop 65 engages the stop bar 69. Once this position is reached, the operator hits the store switch 8d to cause the microprocessor 10 to load deflection data derived from the encoder 22 and load data derived from the load cell 14 into memory. The stop bar 69 is then moved and the wheel is rotated until the stop bar 69 engages stop 66. The store switch 8d is again actuated to record the new load and angle data into memory. This process is repeated for the third angle defined by the third stop 67. When the test is complete, the data can be left in the device's memory, transferred to a personal computer, or printed out.

The hardware and software of the present invention offer various advantages over prior art spring testing equipment. As indicated above, the use of interchangeable load cell cartridges 100 enable the user to quickly switch from one load cell range to another. Also, load cell calibration only requires the cartridge rather than the entire machine. Interchangeable tooling and the rapidity with which tooling changes can be made without special equipment greatly increases efficiency. Further, the apparatus is able to perform two-point testing and an automatic spring rate calculation based upon the change in torque and the change in angle. The apparatus is designed so the user can specify a range or tolerance for either load or deflection angle. As springs are tested against the specified range or tolerance, the display indicates whether the measurement for the spring is too low, acceptable, or too high.

The foregoing description is not intended to be limiting. Instead, it is intended to provide a description of the preferred embodiment sufficient to enable those skilled in the art to practice the invention, the scope of which will be defined by the claims of the patent.

What is claimed is:

1. A torsion spring tester comprising:
   (a) a carriage;
   (b) a first housing mounted to said carriage;
   (c) a second housing slidably mounted to said carriage;
   (d) a load cell located within one of said housings to generate signals representative of torque;
   (e) a first tooling member coupled to the housing in which the load cell is located, said tooling member including a first blank and a first engagement member projecting from said first blank, said tooling member being mounted so that loads applied to the engagement member are sensed by the load cell;
   (f) a second tooling member coupled to the other of said housings, said second tooling member including a second blank and a second engagement member projecting from the second blank;
   (g) a mandrel projecting from the center of one of said first and second blanks;
   (h) an encoder located within one of said first and second housings and coupled to the electronics package to generate signals representative of angular deflection of said first tooling member and said second tooling member as one of said first and second tooling members is rotated; and
   (i) an electronics package for controlling the output of test data, the electronics package coupled to the encoder to receive signals representative of angular deflection and coupled to the load cell to receive signals representative of torque, wherein said electronics package compensates for a deflection of said first tooling member during testing.

2. The apparatus of claim 1 further including a zeroing pin coupled to one of said first and second tooling members for mating with a zeroing slot associated with the other of said first and second tooling members, and means for sending a signal to the electronics package when the zeroing pin is mated with the zeroing slot.

3. The apparatus of claim 1 wherein the housing in which the load cell is mounted includes a face plate fixed to a tube, a bar projecting from said tube, and a flexible metal strip coupling said load cell to said bar.

4. The apparatus of claim 1 further including a flexure and at least one strain gauge to which loads on the load cell are transferred.

5. The apparatus of claim 1 further including means for releasably securing one of said tooling members to one of said housings so that said one of said tooling members can be removed and replaced by another tooling member.

6. The apparatus of claim 5 wherein said means for releasably securing one of said tooling members to one of said housings includes a threaded bore in the blank of the tooling member to be secured and a threaded shaft coupled to a knob, said shaft projecting through a channel in said housing.

7. The apparatus of claim 1 wherein said electronics package includes means for receiving signals generated by said load cell and said encoder, means for processing a signal received from said load cell and said encoder, memory, and means for displaying data.

8. A torsion tester, comprising:
   (a) a load cell to generate signals representative of torque;
   (b) a first tooling member configured to engage a test object and coupled to the load cell, wherein loads applied to the first tooling member are sensed by the load cell;
   (c) a second tooling member configured to engage the test object;
   (d) an encoder for generating signals representative of the angular deflection between said first tooling member and said second tooling member as one of said first and second tooling members is rotated to create an angular deflection in the test object; and
   (e) an electronics package coupled to the encoder to receive signals representative of the angular deflection and coupled to the load cell to receive signals representative of the torque, wherein the electronics package compensates for a deflection of said first tooling member as the load is transferred to the load cell.

9. The apparatus of claim 7 wherein said electronics package calculates spring rate based upon changes torque reflected in signals received from the load cell and changes in angle based upon signals received from the encoder.

10. The apparatus of claim 7 wherein said electronics package is programmable so that a range of acceptable loads can be stored in memory.

11. The apparatus of claim 10 wherein said electronic package indicates whether a tested spring falls within said range or outside of said range.

12. The apparatus of claim 7 wherein said electronics package is programmable so that a range of acceptable deflection angles can be stored in memory.

13. The apparatus of claim 12 wherein said electronic package indicates whether a tested spring falls within said range of acceptable deflection angles.

14. The apparatus of claim 1 wherein said load cell is mounted within an interchangeable cartridge positionable within one of said housings.

15. The apparatus of claim 14 wherein said cartridge includes memory means for holding data related to the performance characteristics of said cartridge and means for conveying said data to said electronics package.

16. The apparatus of claim 15 wherein said performance characteristics held in memory include the full scale value of said cartridge.

17. The apparatus of claim 15 wherein said performance characteristics held in memory include the electrical output of said load cell when zero load is applied to the cell and the electrical output of said load cell when a load approximating the full scale value of said load cell is applied to the load cell.

18. The apparatus of claim 15 wherein said performance characteristics held in memory include data used by the apparatus to linearize the output of the load cell.

19. A torsion tester, as in claim 8, wherein the electronics package calculates the deflection of the first tooling member using an algorithm.

* * * * *